US007945303B2

(12) United States Patent  
Bates et al.

(10) Patent No.: US 7,945,303 B2
(45) Date of Patent: May 17, 2011

(54) NONINVASIVE PULMONARY PERFORMANCE MEASUREMENT METHOD AND SYSTEM

(75) Inventors: Jason H. T. Bates, Essex Junction, VT (US); Charles G. Irvin, Colchester, VT (US); Lennart K. A. Lundblad, Essex Junction, VT (US); John Thompson-Figueroa, Burlington, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 1249 days.

(21) Appl. No.: 11/197,288

(22) Filed: Aug. 3, 2005

(65) Prior Publication Data

US 2006/0030770 A1 Feb. 9, 2006

Related U.S. Application Data

(60) Provisional application No. 60/598,583, filed on Aug. 3, 2004.

(51) Int. Cl.
*A61B 5/05* (2006.01)
(52) U.S. Cl. .......................... 600/407; 600/300; 600/310
(58) Field of Classification Search .......... 600/407–480, 600/300, 301, 310, 322, 323, 324, 547
See application file for complete search history.

(56) References Cited

U.S. PATENT DOCUMENTS

| | | | | |
|---|---|---|---|---|
| 4,383,533 A * | 5/1983 | Lovelace et al. | ............... | 600/437 |
| 5,022,261 A * | 6/1991 | Wolfson et al. | ................. | 73/149 |
| 5,178,151 A * | 1/1993 | Sackner | ........................ | 600/485 |
| 5,273,041 A * | 12/1993 | Richards et al. | ............... | 600/411 |
| 5,379,777 A | 1/1995 | Lomask | ......................... | 128/716 |
| 5,680,871 A * | 10/1997 | Ganshorn | ..................... | 600/533 |
| 5,951,476 A * | 9/1999 | Beach | ............................. | 600/437 |
| 6,175,755 B1 * | 1/2001 | Hogg et al. | .................... | 600/407 |
| 6,298,260 B1 * | 10/2001 | Sontag et al. | ................. | 600/413 |
| 6,352,517 B1 * | 3/2002 | Flock et al. | .................... | 600/595 |
| 6,580,937 B2 * | 6/2003 | Ho et al. | ........................ | 600/415 |
| 6,723,055 B2 * | 4/2004 | Hoffman | ....................... | 600/538 |
| 7,094,206 B2 | 8/2006 | Hoffman | | |
| 2004/0092815 A1 * | 5/2004 | Schweikard et al. | ......... | 600/425 |

OTHER PUBLICATIONS

Mori et al., "Accurate Contiguous Sections Without Breath-Holding on Chest CT: Value of Respiratory Gating and Ultrafast CT", 1994, American Journal of Roentgenology, vol. 162, 1057-1062.*
Schlesinger et al., "Estimation of Total Lung Capacity from Chest Radiography and Chest CT in Children: Comparison with Body Plethysmography", 1995, American Journal of Roentgenology, vol. 165, 151-154.*

* cited by examiner

*Primary Examiner* — Brian Casler
*Assistant Examiner* — Nasir Shahrestani
(74) *Attorney, Agent, or Firm* — Downs Rachlin Martin PLLC

(57) ABSTRACT

A system and method for measuring a pulmonary performance value of a subject. In one embodiment, a system includes one or more imaging devices, each configured to capture one or more images of a subject inside an interior chamber, such as a plethysmograph chamber. An exemplary system also includes an imaging processor in communication with the one or more imaging devices for estimating a change in volume of the subject from information about the one or more images.

36 Claims, 6 Drawing Sheets

NONINVASIVE PULMONARY PERFORMANCE MEASUREMENT METHOD AND SYSTEM

RELATED APPLICATION DATA

This application claims the benefit of U.S. Provisional Patent Application No. 60/598,583, filed Aug. 3, 2004, entitled "Noninvasive Airway Resistance Measurement Method and System," which is incorporated herein by reference in its entirety.

GOVERNMENT LICENSE RIGHTS

The U.S. Government may have a paid-up license in this invention and the right in limited circumstances to require the patent owner to license others on reasonable terms as provided for by the terms of Grant No. HL67273 awarded by National Institutes of Health.

FIELD OF THE INVENTION

The present invention generally relates to the field of pulmonary measurement. In particular, the present invention is directed to a system and method for measuring pulmonary performance.

BACKGROUND OF THE INVENTION

Changes in the caliber (diameter) of the airways of the lung may accompany a number of respiratory diseases, and may have important consequences for a patient. An example of such a change is the airway narrowing that occurs during an acute attack of asthma, when a subject may experience great difficulty in breathing. During such occasions, the flow resistance of the airways increases substantially. Measuring this resistance thus gives a functional assessment of airway narrowing, and is therefore useful as a gauge of disease severity or the efficacy of treatment.

There have been many studies of ways to measure airway resistance in both humans and experimental animals. A standard clinical method for measuring airway resistance in humans includes having a subject perform special breathing maneuvers while inside a closed chamber called a plethysmograph. This type of procedure is often not possible with experimental animals and young children (e.g., those below about 5 years of age). The other standard clinical test of lung function is to have the subject take a deep breath and then exhale as forceably as possible. The amount of air exhaled in a set period of time is sensitive to the presence of certain lung diseases, but is only loosely related to actual airway resistance. This approach again is difficult in animals and young children, although it is employed in sedated infants by subjecting them to a whole-body squeeze designed to force air out of the lungs. In the case of animals, the standard approach is to measure airway resistance using invasive procedures that procure the necessary pressure and flow signals. These methods are accurate, but invariably either harm the animal or at the very least place it under unnatural circumstances that likely affect the resistance measurements obtained.

There is, thus, a great need for a means of measuring airway resistance that is both convenient and noninvasive, for use with all subjects (including young humans and experimental animals). Such a method currently does not exist, despite the widespread use of surrogates based purely on the measurement of the pattern of breathing (i.e., volume inspired per breath and rate of breathing).

SUMMARY OF THE INVENTION

One aspect of the present invention includes an imaging system for a plethysmograph. The system includes one or more imaging devices, wherein each of the one or more imaging devices is operatively configured to capture one or more images of a subject inside the plethysmograph as the subject breathes one or more gases and/or aerosols contained within the plethysmograph and operable to provide an output signal including information regarding the one or more images. The system also includes an imaging processor in communication with the one or more imaging devices and operatively configured to estimate a change in volume of the subject from the information.

Another aspect of the present invention includes a plethysmograph for a non-invasive pulmonary measurement of a subject. The plethysmograph includes a structure having an interior chamber for receiving the subject and for containing one or more gases. The plethysmograph also includes one or more imaging devices, wherein each of the one or more imaging devices captures one or more images of the subject, when positioned in the structure, as the subject breathes the one or more gases and provides an output signal including information regarding the one or more images. Further, the plethysmograph includes an imaging processor in communication with the one or more imaging devices so as to receive the output signal, wherein the imaging processor estimates a change in volume of the subject using the information included in the output signal.

Yet another aspect of the present invention includes a noninvasive system for measuring changes in pulmonary airway resistance of a subject. The system includes a structure having an interior chamber for receiving the subject and for containing one or more gases. Further, the system includes a pressure sensor for measuring a pressure of the one or more gases. Still further, the system includes one or more imaging devices, wherein each of the one or more imaging devices captures one or more images of the subject as the subject breathes the one or more gases and provides an output signal including information about the one or more images. Yet further, the system includes an imaging processor in communication with the one or more imaging devices so as to receive the output signal, wherein the imaging processor estimates a change in volume of the subject using the information included in the output signal.

Still another aspect of the present invention includes a method of measuring changes in pulmonary airway resistance of a subject. The method includes (a) enclosing the subject and one or more gases within a compartment; (b) obtaining one or more images of the subject as the subject breathes the one or more gases; and (c) estimating a change in volume of the subject from the one or more images.

Still yet another aspect of the present invention includes a method of retrofitting a plethysmograph. The method includes (a) positioning one or more imaging devices such that each of the one or more imaging devices is operatively configured to capture one or more images of a subject inside the plethysmograph as the subject breathes one or more gases contained within the plethysmograph and operable to provide information regarding the one or more images; and (b) providing an imaging processor in communication with the one or more imaging devices, the imaging processor being for processing the information to estimate a change in volume of the subject.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION

The present invention includes the use of an imaging device and an image processor to determine a change in volume measurement of a subject positioned in an interior chamber of a structure that encloses the subject and one or more gases. The change in volume measurement may be used to calculate a pulmonary performance value, such as an airway resistance value.

Figure 1:
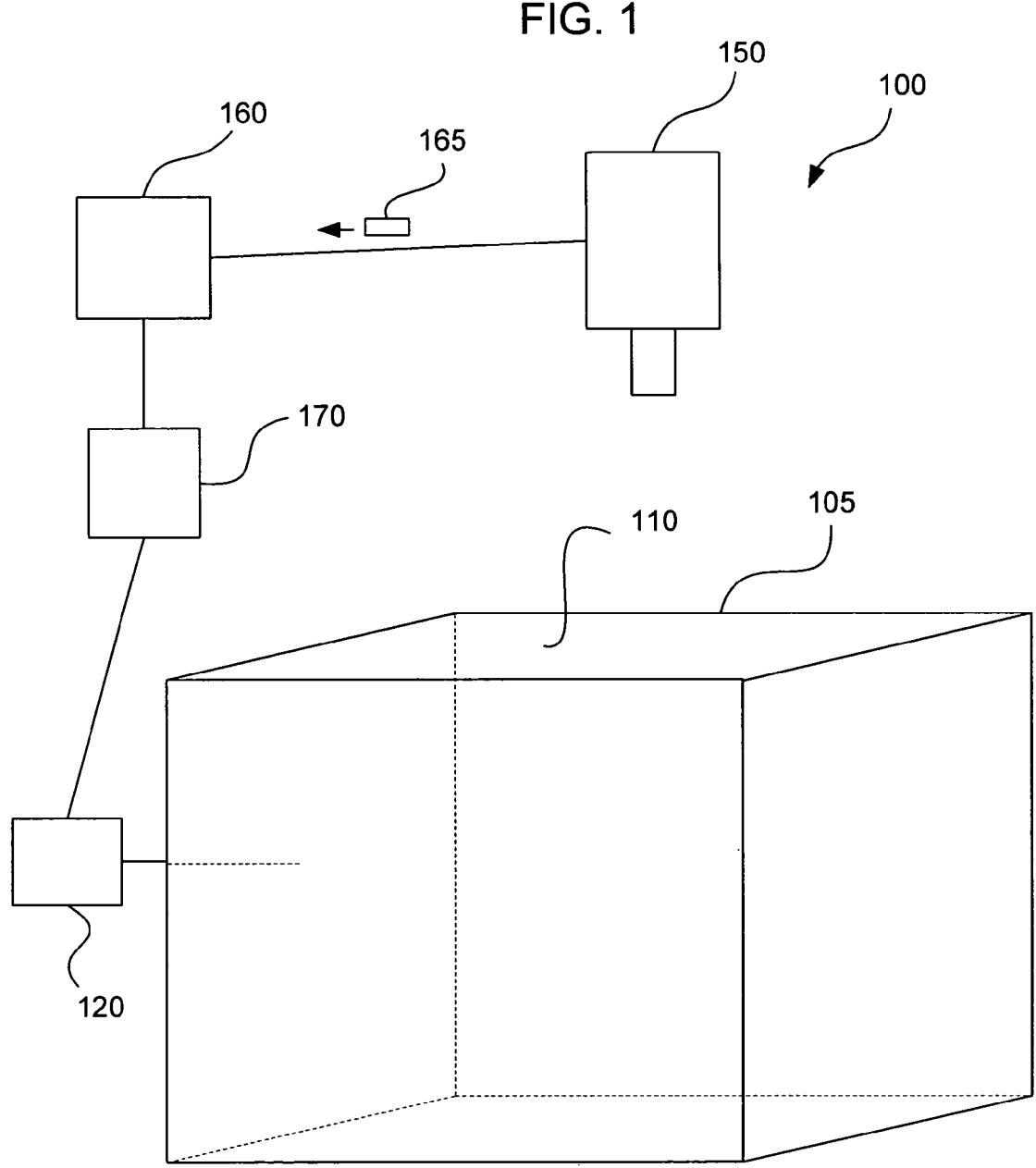
FIG. 1 shows one exemplary embodiment of a system according to the present invention.

Referring now to FIG. 1, an exemplary embodiment of the present invention is illustrated. A system 100 includes a structure 105 having an interior chamber 110. Interior chamber 110 is configured for receiving a subject (not shown) and containing one or more gases therein. System 100 also includes a pressure sensor 120 for detecting a pressure of the one or more gases within the interior chamber 110. An imaging device 150 is positioned to capture an image of a subject that is within interior chamber 110 while the subject breathes the one or more gases. An imaging processor 160 is in communication with imaging device 150. Imaging device 150 provides an output signal 165 to imaging processor 160. Output signal 165 includes information regarding the image of the subject. Imaging processor 160 estimates a change in volume of the subject using the information about a plurality of images of the subject.

In one example, imaging device 150 captures a plurality of images over time while the subject breathes the one or more gases. Each of the plurality of images shows a contrast between the subject and the background. Imaging processor 160 uses an algorithm that compares the number of pixels representing the subject in one image to the number of pixels of the subject in another image. Depending on the estimated shape of the subject, the pixels are correlated to represent a volume of the subject. For example, a subject that is substantially cylindrical in shape would have its image pixels extrapolated differently by an algorithm than a cuboidally shaped subject. The algorithm may also take into account the uniformity or lack of uniformity of expansion of the subject during inspiration. Construction of such algorithms are well known to those of ordinary skill. In this example, the difference in volume is correlated to a change in volume that is indicative of a tidal volume, VT. A tidal volume can be used with an inspiration plethysmographic pressure integral (IPPI), shown in Equation 1 below, to determine an airway resistance value, $R_{AW}$, as shown by Lundblad, L. et al., "A reevaluation of the validity of unrestrained plethysmography in mice," J Appl Physiol 93: 1198-1207, 2002, which is incorporated herein by reference as if set forth in its entirety. The IPPI can be shown as follows:

$$IPPI = \int_0^{Ti} P_b(t) dt = \frac{V_T R_{aw} FRC}{V_b},  \quad (1)$$

where $P_b(t)$ is the pressure of the one or more gases in internal chamber 110 (relative to atmospheric pressure), FRC is a functional residual capacity, and $V_b$ is the volume of the one or more gases within internal chamber 110.

A subject to be studied using a system according to the present invention, such as system 100, may include any living creature. Example subjects include, but are not limited to, an animal, such as a laboratory animal; a human; and any combination thereof. In one example, the subject is a human child. In another example, the subject is a non-ambulatory human adult. In yet another example, the subject is a laboratory mouse.

The one or more gases according to the present invention may include any gas that a live subject is capable of breathing. Examples of such gases include, but are not limited to, air, oxygen, and non-toxic mixtures of gases including oxygen. In one aspect, one or more gases may be maintained at a temperature that is about the temperature of a pulmonary airway of the subject. In another aspect, one or more gases may be maintained at a level of humidity that is about the humidity of a pulmonary airway of the subject. In yet another aspect, both the temperature and the humidity may be maintained.

An imaging device, such as imaging device 150, according to the present invention can be any device capable of capturing one or more images of a subject within a closed compartment, such as internal chamber 110, from which an estimate of change in volume can be calculated. The one or more images may include detailed information regarding the subject at one or more points in time. The one or more images may include a color image, a black and white image, a silhouette of the subject, an indication of a position of a marking on the subject (such as a thoracic marking), and any combinations thereof. Example imaging devices include but are not limited to, a camera, an x-ray imager, and any combinations thereof. In one example, an imaging device includes a camera. An imaging device may capture images at a certain rate that may be fixed or variable, depending on the circumstances. In one example, an imaging device has an image capture rate of about 48 frames per second (fps). Faster image acquisition capability may increase the reliability of a system to estimate changes in volume of a subject as the subject breathes the one or more gases within internal chamber 110. An imaging device may also have any resolution capable of producing one or more images that translate into a reasonably accurate volume change calculation. The resolution may impact the volume calculation. In one example, the resolution of an image captured by an imaging device, such as imaging device 150, impacts the number of pixels that may be used by imaging processor 160 to calculate a change in volume. In another example, imaging device 150 includes a 1 megapixel, black and white, charged coupled device (CCD) camera.

System 100 shows one imaging device 150. However, a system and method according to the present invention may include a plurality of imaging devices for capturing one or more images of a subject from different angles. In one example, one imaging device is utilized to capture one or more images of a subject that is substantially cylindrical in body form and has a substantially uniform expansion during intake and outtake of the one or more gases. Although one imaging device may be used with non-cylindrical subjects or subjects that have non-uniform expansion during inspiration, more than one camera may increase the reliability of an estimate of change in volume. In another example, two imaging devices may be used in an orthogonal (or other) position to each other with respect to the subject within internal chamber 110 of structure 105. In one aspect, imaging processor 160 may include computed tomography (CT) technology for processing one or more images from each of the two imaging devices for estimating a change in volume of the subject. In yet another example, three or more imaging devices may be used in conjunction with CT technology to estimate a change in volume of the subject. Any number of imaging devices may be used so long as an estimate of change in volume of a subject that is accurate enough for the particular purposes can be ascertained from the one or more images captured by the imaging device or devices. One or more imaging devices, such as imaging device 150, may be positioned outside interior chamber 110, as shown in FIG. 1; inside interior chamber 110; or a combination of inside and outside interior chamber 110.

Structure 105 is shown in FIG. 1 as having a cubiodal shape. Structure 105 may take any shape and/or form that is capable of enclosing a subject and the one or more gases therein. The shape and size of structure 105 and the interior chamber 110 may depend on the size and shape of the subject to be studied therein. Structure 105 may be constructed of any material or combination of materials that will allow a subject to be received therein and one or more gases to be contained therein. At least one side of structure 105 should be configured to allow imaging device 150 to capture one or more images of a subject within interior chamber 110. In one example, a side of structure 105 includes a transparent material that allows a subject therein to be visualized by an imaging device positioned to capture an image of the subject through that side. Where a plurality of imaginging devices are utilized, more than one side of structure 105 may be constructed of a material that allows an imaging device to capture one or more images of a subject therein.

Structure 105 may be a plethysmograph chamber. One example of a plethysmograph chamber is described in U.S. Pat. No. 5,379,777 to Lomask, which is incorporated herein by reference as if set forth in its entirety. However, a variety of general plethysmograph chamber configurations are known to those of ordinary skill. Structure 105 may include a door, a hatch, or other closeable opening (not shown) configured in one or more of its sides for allowing a subject to be received within interior chamber 110. Structure 105 may also include optional closeable ports (not shown) for a variety of functions including, but not limited to, venting interior chamber 110; passing an object, such as water or food, into interior chamber 110; passing wires to monitoring devices within the chamber or tubes for delivering fluids; inserting temperature or humidity probes; and any combinations thereof. An interior surface (not shown) of structure 105 may be configured such that it provides adequate contrast to a subject within interior chamber 110 when one or more images are captured by imaging device 150. In one example, an interior surface may include a material of a color that provides such contrast. In another example, a material (not shown) for providing contrast may be positioned on or near a wall of structure 105.

Imaging processor 160 may be any device capable of estimating a change in volume of a subject within interior chamber 110 from information representing one or more images of the subject. In one example, an image processor may include an algorithm for estimating a change in volume. In another example, an image processor may include CT technology. Examples of an image processor include, but are not limited to, a general computing device, a dedicated microprocessor, and any combinations thereof. Referring again to FIG. 1, system 100 includes an optional pulmonary calculation module 170 in communication with imaging processor 160 and pressure sensor 120. Although, pulmonary calculation module 170 is shown separate from imaging processor 160, pulmonary calculation module 170 may alternatively be included within imaging processor 160. Pulmonary calculation module 170 is configured to receive one or more change in volume values from imaging processor 160, either by way of internal communication within imaging processor 160 or via an external connection as shown in FIG. 1. Pulmonary calculation module 170 is also configured to process the one or more change in volume values to provide a pulmonary performance value. In one example, pulmonary calculation module 170 is also configured to receive one or more pressure measurement values from pressure sensor 120 and to use the one or more change in volume values with Equation (1) from above to calculate an airway resistance value.

Although one or more embodiments herein show a system and/or method for measuring an airway resistance, the present invention may be used effectively for other pulmonary measurements of subjects where change in volume measurements of the subject are needed. Examples of such other applications include, but are not limited to, and any combinations thereof.

Figure 2:
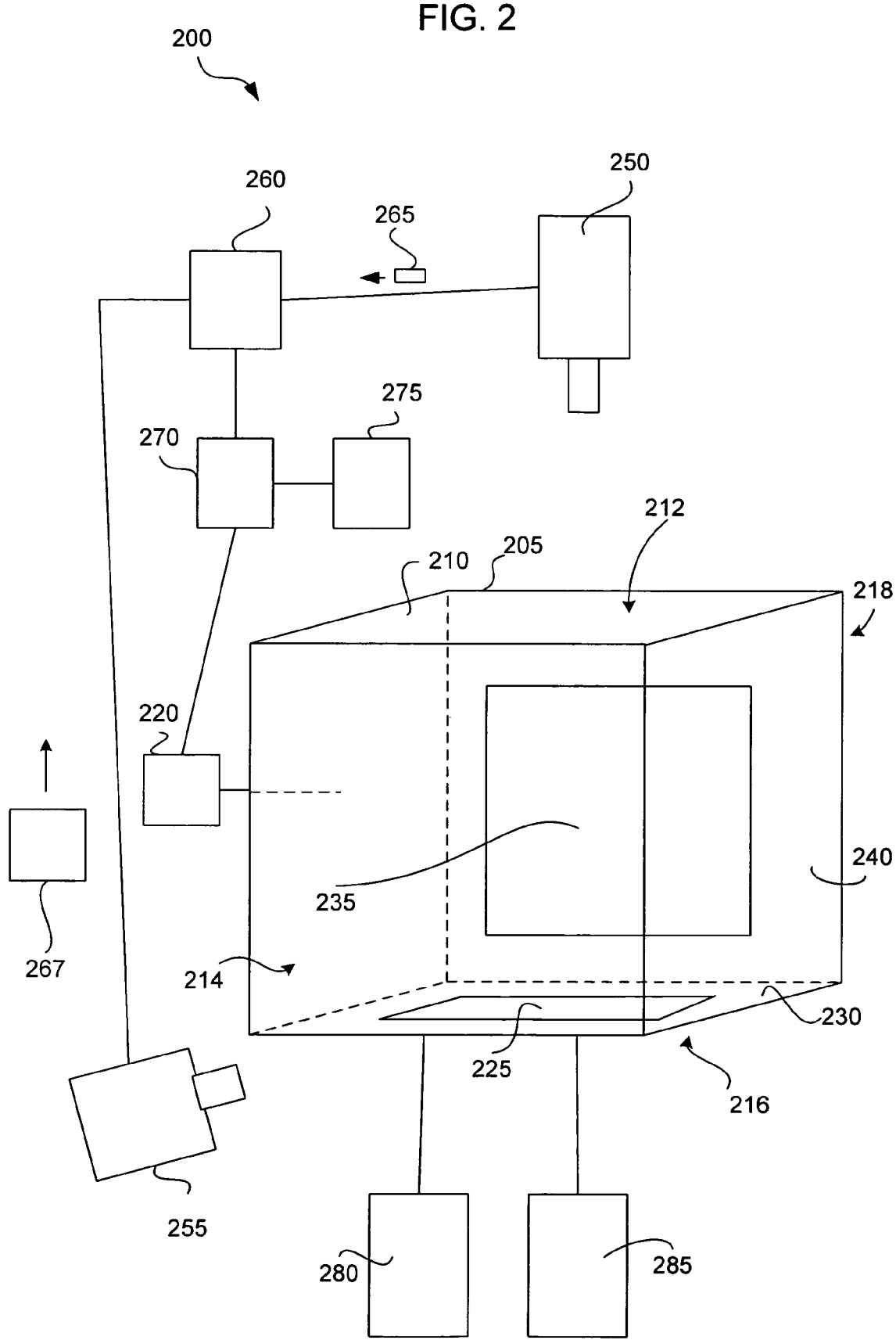
FIG. 2 shows an exemplary embodiment of a system according to the present invention.

FIG. 2 illustrates another exemplary embodiment according to the present invention. System 200 includes a structure 205 having an interior chamber 210. Structure 205 includes a first side 212, a second side 214, a third side 216, and a fourth side 218, respectively. Interior chamber 210 is configured for receiving a subject and containing one or more gases therein. System 200 also includes a pressure sensor 220 for detecting a pressure of the one or more gases within interior chamber 210. A first imaging device 250 is positioned to capture one or more images of a subject that is within interior chamber 210 while the subject breathes the one or more gases. First imaging device 250 is positioned confronting first side 212. A second imaging device 255 is positioned to capture one or more images of the subject from a second angle. Second imaging device 255 is positioned confronting second side 214. A first contrast assistance element 225 is positioned on an interior surface 230 of third side 216. This positions first contrast assistance element 225 so that a subject received within interior chamber 210 would be between first imaging device 250 and first contrast assistance element 225. A second contrast assistance element 235 is positioned on an interior surface 240 of fourth side 218. This positions second contrast assistance element 235 so that a subject received within interior chamber 210 would be between second imaging device 255 and second contrast assistance element 235. An imaging processor 260 is in communication with imaging devices 250 and 255. First imaging device 250 provides an output signal 265 to imaging processor 260. Second imaging device 255 provides an output signal 267 to imaging processor 260. Output signals 265 and 267 include information regarding the one or more captured images of the subject. Imaging processor 260 estimates a change in volume of the subject using the information about a plurality of images of the subject. By utilizing information from two imaging devices (and optionally more imaging devices), imaging processor 260 may be able to more accurately estimate the change in volume of the subject within interior chamber 210 while the subject breathes the one or more gases therein. Change in volume may be calculated by imaging processor 260 in the same manner imaging processor 160 estimates change in volume except that imaging processor 260 takes into account one or more images from each of first imaging device 250 and second imaging device 255.

Pulmonary calculation module 270 receives one or more change in volume values from imaging processor 260. Pulmonary calculation module 270 is also in communication with pressure sensor 220 for receiving one or more pressure values that reflect the pressure of the one or more gases over time. Pulmonary calculation module 270 processes the one or more change in volume values and one or more pressure values to calculate a pulmonary performance value, such as an airway resistance value. Pulmonary calculation module 270 is in communication with an output device 275 for outputting the pulmonary performance value.

A contrast assistance element, such as contrast assistance elements 225 and 235, may include any material that provides contrast to a subject within interior chamber 210 when one or more images are captured by an imaging device, such as imaging devices 250 and 255. In one example, a contrast assistance element may be directly on a surface of structure 205. This surface may be an interior surface as shown in FIG. 2, or may be an external surface, where the side of structure 210 is constructed of a transparent material. In another example, a contrast assistance element may be positioned near a side of structure 205. In yet another example, a contrast assistance element may be configured with a colored material that contrasts with the subject. In still another example, a contrast assistance element may include a material that actively provides light to increase contrast. Examples of a contrast assistance element include, but are not limited to, an electroluminescent panel, a coating, an LED, another backlighting system, and any combinations thereof.

Referring again to FIG. 2, system 200 includes a temperature regulation element 280 in communication with structure 205 for maintaining a predetermined temperature of the one or more gases within interior chamber 210. Temperature regulation element 280 may be configured to cool the one or more gases, heat the one or more gases, or any combination thereof. Examples of temperature regulation element 280 include, but are not limited to, a water jacket, hot air blower, and any combinations thereof. Temperature regulation element 280 may be an external element to structure 205, may be part of structure 205, or may be an internal element positioned within interior chamber 210. In one example, one or more side walls of structure 210 may be configured as double walls for allowing water of a predetermined temperature to flow therebetween. In one aspect, the temperature of the one or more gases may be maintained at a temperature that is about the temperature of an airway of the subject (e.g., about 98.6° F.).

System 200 also includes a moisture regulation element 285 in communication with structure 205 for maintaining a predetermined level of moisture of the one or more gases within interior chamber 210. Moisture regulation element 285 may be an external element to structure 205, may be part of structure 205, or may be an internal element positioned within interior chamber 210. Examples of a moisture regulation element include, but are not limited to, a wet gauze placed within interior chamber 210, bubbling air through water, a dessicant material, and any combinations thereof. In one aspect, the moisture level of the one or more gases may be maintained at a moisture level that is about the moisture level of an airway of the subject. It may be beneficial to maintain humidity level and temperature of the one or more gases that approximates those of the airway of a subject for certain pulmonary performance value calculations. For example, when using Equation (1) to calculate an airway resistance, it is beneficial for the one or more gases in interior chamber 210 to be saturated with moisture and to be maintained at a temperature that is about the same as that of the airway of a subject within interior chamber 210.

In yet another embodiment of the present invention, an imaging system for a plethysmograph is provided. The imaging system includes one or more imaging devices, such as imaging device 150 of FIG. 1. The imaging system also includes an imaging processor, such as imaging processor 160, in communication with the one or more imaging devices. Such a system may be used to retrofit an existing plethysmograph for estimating a change in volume of a subject therein by positioning one or more imaging devices to capture one or more images of the subject and providing information regarding the one or more images to the imaging processor.

EXAMPLE 1

In this example, a system according to the present invention was constructed and the system was calibrated using a finger of a latex glove (to simulate a subject) into and out of which a known quantity of one or more gases was introduced. A cuboidal plethysmograph chamber with two clear orthogonal sides through which a subject mouse could be visualized was constructed. The two remaining sides incorporated a water jacket to allow for controlled heating of the air within the plethysmograph chamber. A small amount of wet gauze could be placed inside the chamber for maintaining the necessary level of humidity. A piezoresistive pressure transducer was configured in communication with the interior chamber of the plethysmograph chamber for monitoring the pressure of the air within.

A pair of one mega-pixel black&white CCD video cameras were mounted in orthogonal viewing positions, each directed at one of the clear sides of the plethysmograph chamber. The cameras were distanced from the walls of the plethysmograph chamber so as to have their viewing areas completely filled by each of the 50 mm×50 mm chamber walls, giving a linear spatial resolution at the chamber walls of $50/_{1,000}$=0.05 mm. In order to provide good contrast between the video image of the mouse and the background, the inside walls of the chamber opposite each viewing wall were lined with an electroluminescent panel (Proto-Kut™, available from BKL Inc., King of Prussia, Pa.) that can be cut to any desired shape and provide uniform illumination when excited by a small current oscillating at 400 Hz. Each video camera had a frame rate of up to 48 Hz. Images were captured by each camera and acquired by an IMAQ frame grabber controlled by Labview software on an imaging processor that was in communication with the two cameras. The images were analyzed by Vision Builder program on the imaging processor. Each of the IMAQ frame grabber, Labview software and Vision Builder program are available from National Instruments of Austin, Tex.

Figure 3A:
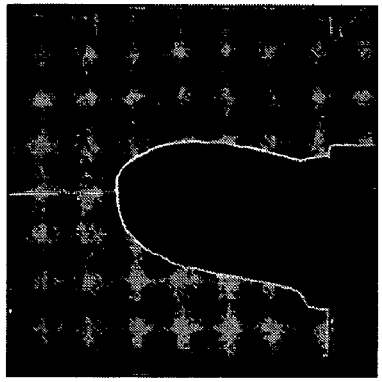
FIG. 3A shows an example of an image of an object within a plethysmograph.
Figure 3B:
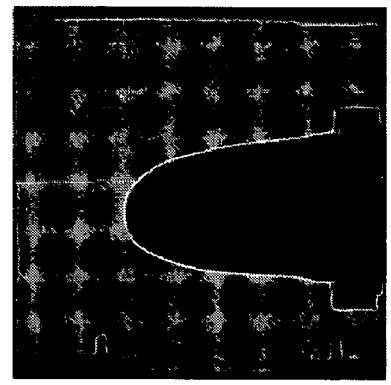
FIG. 3B shows another example of an image of an object within a plethysmograph.
Figure 3C:
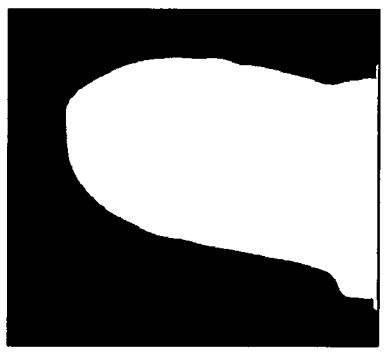
FIG. 3C shows yet another example of an image of an object within a plethysmograph.
Figure 3D:
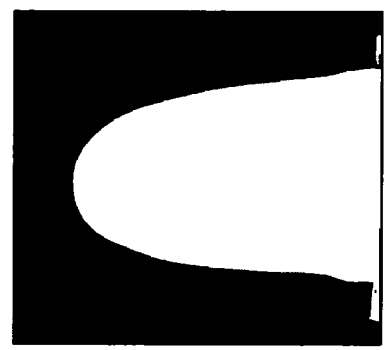
FIG. 3D shows still another example of an image of an object within a plethysmograph.
Figure 4:
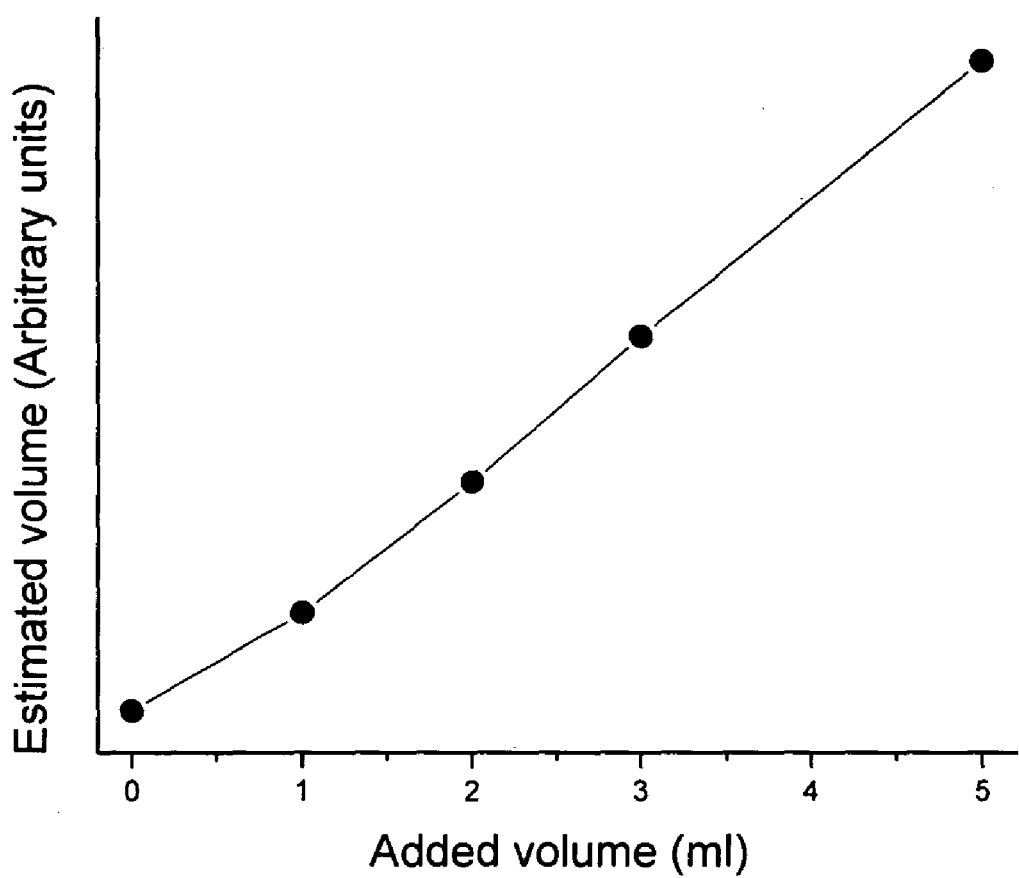
FIG. 4 shows a plot of estimated volumes of an example object within a plethysmograph that were estimated using a system according to the present invention.

The system was calibrated by imaging a finger of a latex glove before and after addition of 5 milliliters (ml) of air in 1 ml increments. The glove finger was positioned within the plethysmograph chamber and connected to a tracheal cannula in a side of the plethysmograph chamber. The tracheal cannula was connected to a device for providing a known quantity of air to the glove finger, such as a FlexiVent manufactured by Scireq Inc. of, Montreal, Quebec. FIGS. 3A and 3B illustrate raw horizontal image (taken from a first of the two imaging devices) and a raw vertical image (taken from a second of the two imaging devices), respectively, of the glove finger. FIGS. 3C and 3D illustrate corresponding horizontal and vertical images after the images were processed in the imaging processor to black and white pixels. The volume of the glove finger was estimated from each of the two images by assuming a circular cross section at each horizontal position along the image. The mean of the two volume estimates was then taken as the final estimate of volume. FIG. 4 illustrates a regression plot of actual volume of air added to the glove finger versus the volume estimated from a change in volume of the glove finger in arbitrary units. The relationship is almost perfectly straight except for a slight upward concavity at the low end of the volume range, which was probably due to the fact that the finger was initially somewhat flaccid and the initial injection of volume was absorbed by buckles in the wall. This demonstrates that imaging system was capable of resolving the types of volume changes expected during spontaneous breathing in a mouse (e.g., in the order of 0.2 ml).

The estimated volume values were scaled such that the regression plot in FIG. 4 had a slope of about 1.0. The scaled plot was used to calibrate the system to true volume measurements for obtaining a calibration factor.

EXAMPLE 2

The calibration factor obtained in EXAMPLE 1 was used to estimate changes of volume in a mouse. A BALB/c mouse was euthanized by overdose of anesthetic and placed immediately in the plethysmograph in the supine position. The mouse was tracheostomized, and the tracheal cannula was sealed through the front wall of the plethysmograph chamber and connected to a 1 ml syringe. Air was injected into and withdrawn from the lungs in 0.2 ml increments up to a total of 1 ml (approximately the vital capacity of the mouse).

Figure 5A:
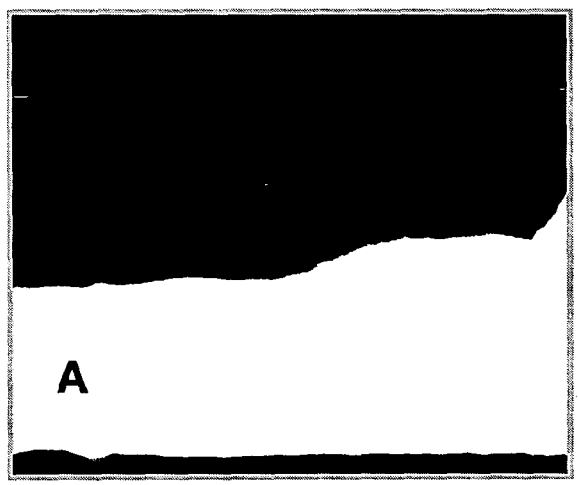
FIG. 5A shows an example of an image of a mouse within a plethysmograph.
Figure 5B:
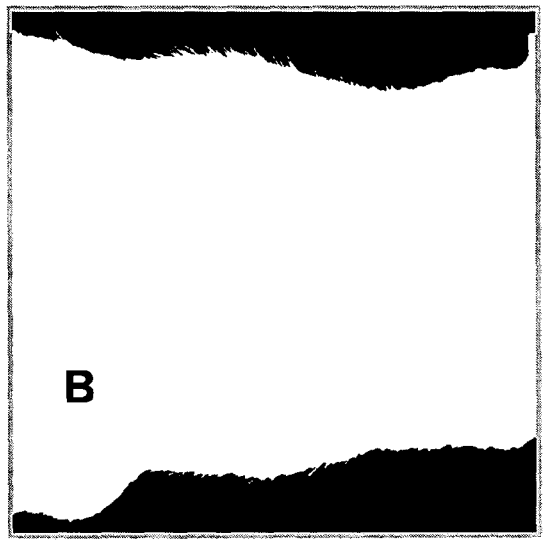
FIG. 5B shows another example of an image of a mouse within a plethysmograph.

FIG. 5A illustrates an example of an image of the mouse thorax from the first camera after thresholding. FIG. 5B illustrates another example of an image of the mouse thorax from the second camera after thresholding. The detailed resolution of the thorax is apparent in the appearance of the animal's fur in the images. Thoracic volume was estimated at each increment by summing the product of the widths of the two images at each point along the axial direction, each product being multiplied by the pixel width estimated from the above calibration experiment with the glove finger.

Figure 6:
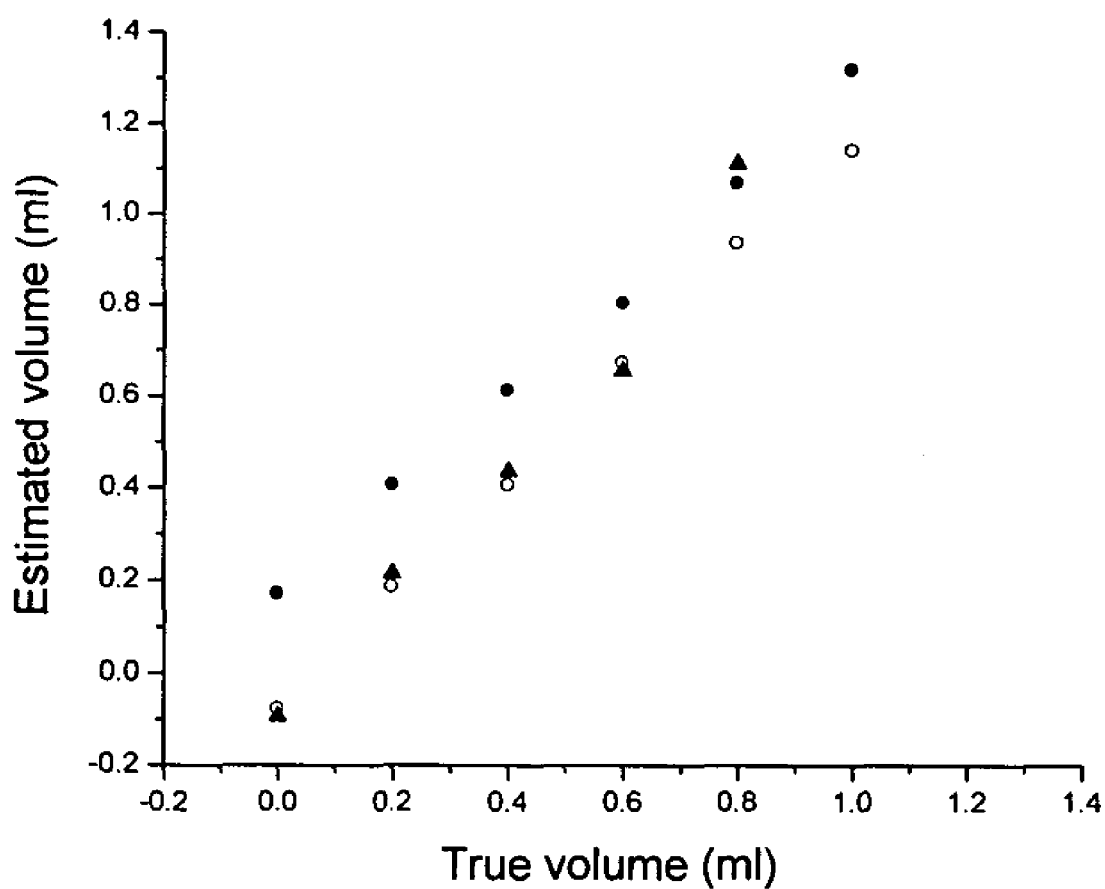
FIG. 6 shows a plot of estimated volumes of an example mouse within a plethysmograph versus actual volumes.

FIG. 6 shows a plot of the estimated volume increments obtained during an inflation, a deflation, and a re-inflation over the 1 ml volume range, each point relative to the initial pre-inflation volume. The three volume sweeps that were produced are linear and reproducible. The total excursion of the regression line fitted to each volume sweep had a mean value of 1.24 ml, which is a little larger than the 1.0 ml actually injected or withdrawn. A somewhat larger estimate is consistent with that which would be expected because the volume estimation algorithm assumed the mouse had a rectangular cross-section, whereas in reality it was more oval.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. An imaging system for a plethysmograph, the system comprising:
   one or more imaging devices, wherein each of said one or more imaging devices is operatively configured to capture one or more images of a subject inside the plethysmograph as the subject breathes one or more gases contained within the plethysmograph and operable to provide an output signal including information regarding said one or more images, said one or more imaging devices including at least two imaging devices positioned orthogonal to each other with respect to the subject;
   a contrast assistance element positioned so as to be opposite at least one of said one or more imaging devices; and
   an imaging processor in communication with said one or more imaging devices and operatively configured to estimate a change in volume of said subject from said information.

2. A system according to claim 1, wherein said imaging processor is a computer.

3. A system according to claim 1, wherein said imaging processor comprises computed tomography technology for estimating said change in volume.

4. A plethysmograph for a non-invasive pulmonary measurement of a subject, the plethysmograph comprising:
   a structure having an interior chamber for receiving the subject and for containing one or more gases;
   one or more imaging devices, wherein each of said one or more imaging devices captures one or more images of the subject, when positioned in the structure, as the subject breathes said one or more gases and provides an output signal including information regarding said one or more images, said one or more imaging devices including at least two imaging devices positioned orthogonal to each other with respect to the subject; and
   an imaging processor in communication with said one or more imaging devices so as to receive said output signal, wherein said imaging processor estimates a change in volume of the subject using said information included in said output signal, wherein said structure includes an inside surface defining a portion of said interior chamber, said plethysmograph further including a contrast assistance element positioned on said inside surface so as to be opposite said one or more imaging devices.

5. A plethysmograph according to claim 4, wherein said one or more imaging devices is inside said interior chamber.

6. A plethysmograph according to claim 4, wherein said one or more imaging devices is outside said interior chamber.

7. A plethysmograph according to claim 4, further comprising a temperature regulation element for maintaining a temperature of said one or more gases at or about the temperature of a pulmonary airway of the subject.

8. A plethysmograph according to claim 4, further comprising a moisture regulation element for maintaining a predetermined level of moisture of said one or more gases.

9. A plethysmograph according to claim 4, wherein said contrast assistance element comprises an electroluminescent panel.

10. A plethysmograph according to claim 4, wherein said imaging processor is a computer.

11. A plethysmograph according to claim 4, wherein said imaging processor comprises computed tomography technology for estimating said change in volume.

12. A plethysmograph according to claim 4, further comprising a corralling element positioned in said structure and operatively configured to position the subject in a field of view of said one or more imaging devices.

13. A plethysmograph according to claim 4, further comprising a pressure sensor for measuring a pressure of said one or more gases.

14. A plethysmograph according to claim 13, further comprising an pulmonary calculation module in communication with said pressure sensor and said imaging processor, wherein said pulmonary calculation module calculates a pulmonary performance value from a plurality of said change in volume estimates and said pressure measurements.

15. A plethysmograph according to claim 14, wherein said pulmonary performance value includes an airway resistance value.

16. A noninvasive system for measuring changes in pulmonary airway resistance of a subject, the system comprising:
- a structure having an interior chamber for receiving the subject and for containing one or more gases;
- a pressure sensor for measuring a pressure of said one or more gases;
- one or more imaging devices, wherein each of said one or more imaging devices captures one or more images of the subject as the subject breathes said one or more gases and provides an output signal including information about said one or more images, said one or more imaging devices including at least two imaging devices positioned orthogonal to each other with respect to the subject; and
- an imaging processor in communication with said one or more imaging devices so as to receive said output signal, wherein said imaging processor estimates a change in volume of the subject using said information included in said output signal, wherein said structure includes an inside surface defining a portion of said interior chamber, said system further including a contrast assistance element positioned on said inside surface so as to be opposite said one or more imaging devices.

17. A system according to claim 16, wherein said one or more gases is maintained at a moisture level that is about the moisture level of a pulmonary airway of the subject and at a temperature that is about the temperature of said pulmonary airway.

18. A system according to claim 16, further comprising a temperature regulation element for maintaining a temperature of said one or more gases at or about the temperature of a pulmonary airway of the subject.

19. A system according to claim 16, further comprising a moisture regulation element for maintaining a predetermined level of moisture of said one or more gases.

20. A system according to claim 16, wherein said contrast assistance element comprises an electroluminescent panel.

21. A system according to claim 16, further comprising a corralling element positioned in said structure and operatively configured to position the subject in a field of view of said one or more imaging devices.

22. A system according to claim 16, further comprising a pulmonary calculation module in communication with said pressure sensor and said imaging processor, wherein said pulmonary calculation module calculates a pulmonary performance value from a plurality of said change in volume estimates and said pressure measurements.

23. A system according to claim 16, wherein said pulmonary performance value includes an airway resistance value.

24. A method of measuring changes in pulmonary airway resistance of a subject, the method comprising:
- enclosing the subject and one or more gases within a compartment;
- obtaining one or more images of the subject as the subject breathes said one or more gases, said obtaining using one or more imaging devices including at least two imaging devices positioned orthogonal to each other with respect to the subject, and using a contrast assistance element positioned so as to be opposite at least one of said one or more imaging devices; and
- estimating a change in volume of said subject from said one or more images.

25. A method according to claim 24, further comprising measuring a pressure of said one or more gases within said compartment as the subject breathes.

26. A method according to claim 25, further comprising calculating an airway resistance value from a plurality of said change in volume estimates and pressure measurements.

27. A method of retrofitting a plethysmograph, the method comprising:
- positioning one or more imaging devices such that each of said one or more imaging devices is operatively configured to capture one or more images of a subject inside the plethysmograph as said subject breathes one or more gases contained within the plethysmograph and operable to provide information regarding said one or more images, said one or more imaging devices including at least two imaging devices positioned orthogonal to each other with respect to the subject;
- positioning a contrast assistance element on an inside surface of the plethysmograph, said inside surface being opposite said one or more imaging devices; and
- providing an imaging processor in communication with said one or more imaging devices, said imaging processor being for processing said information to estimate a change in volume of said subject.

28. A method according to claim 27, wherein said imaging processor includes a pulmonary calculation module for calculating an airway resistance value from said change in volume.

29. An imaging system for a plethysmograph, the system comprising:
- one or more imaging devices, wherein each of said one or more imaging devices is operatively configured to capture one or more images of a subject inside the plethysmograph as the subject breathes one or more gases contained within the plethysmograph and operable to provide an output signal including information regarding said one or more images;
- an imaging processor in communication with said one or more imaging devices and operatively configured to estimate a change in volume of said subject from said information; and
- a contrast assistance element configured to be positioned opposite at least one of said one or more imaging devices.

30. An imaging system for a plethysmograph according to claim 29, wherein said contrast assistance element comprises an electroluminescent panel.

31. A plethysmograph for a non-invasive pulmonary measurement of a subject, the plethysmograph comprising:
- a structure having an interior chamber for receiving the subject and for containing one or more gases;

one or more imaging devices, wherein each of said one or more imaging devices captures one or more images of the subject, when positioned in the structure, as the subject breathes said one or more gases and provides an output signal including information regarding said one or more images;

a contrast assistance element positioned so as to be opposite at least one of said one or more imaging devices; and an imaging processor in communication with said one or more imaging devices so as to receive said output signal, wherein said imaging processor estimates a change in volume of the subject using said information included in said output signal.

32. A plethysmograph according to claim 31, wherein said contrast assistance element comprises an electroluminescent panel.

33. A method of measuring changes in pulmonary airway resistance of a subject, the method comprising:

enclosing the subject and one or more gases within a compartment, the compartment including a contrast assistance element positioned proximate an inside surface of the compartment;

obtaining one or more images of the subject as the subject breathes said one or more gases; and estimating a change in volume of said subject from said one or more images.

34. A method according to claim 33, further comprising measuring a pressure of said one or more gases within said compartment as the subject breathes.

35. A method according to claim 34, further comprising calculating an airway resistance value from a plurality of said change in volume estimates and pressure measurements.

36. A method of retrofitting a plethysmograph, the method comprising:

positioning one or more imaging devices such that each of said one or more imaging devices is operatively configured to capture one or more images of a subject inside the plethysmograph as said subject breathes one or more gases contained within the plethysmograph and operable to provide information regarding said one or more images;

positioning a contrast assistance element proximate a surface of the plethysmograph so as to be opposite at least one of said one or more imaging devices; and providing an imaging processor in communication with said one or more imaging devices, said imaging processor being for processing said information to estimate a change in volume of said subject.

* * * * *